(12) United States Patent
Lin

(10) Patent No.: US 6,316,033 B1
(45) Date of Patent: Nov. 13, 2001

(54) COMPOSITIONS FOR TREATMENT OF ANTIBIOTIC-RESISTANT GRAM-POSITIVE BACTERIAL INFECTIONS AND METHODS FOR USING AND PREPARING THE SAME

(75) Inventor: Yuan Lin, Bethesda, MD (US)

(73) Assignee: Marco Polo Technologies, Bethesda, MD (US)

( * ) Notice: Subject to any disclaimer, the term of this patent is extended or adjusted under 35 U.S.C. 154(b) by 0 days.

(21) Appl. No.: 09/406,804

(22) Filed: Sep. 28, 1999

Related U.S. Application Data

(62) Division of application No. 09/138,127, filed on Aug. 24, 1998, now Pat. No. 6,025,400.

(51) Int. Cl.[7] .................................................. A61K 35/78
(52) U.S. Cl. .......................................... 424/773; 424/725
(58) Field of Search ...................... 424/773, 725

(56) References Cited

U.S. PATENT DOCUMENTS

| | | | |
|---|---|---|---|
| 4,202,877 | 5/1980 | Sato | 424/43 |
| 5,466,452 | 11/1995 | Whittle | 424/195.1 |
| 5,547,674 | 8/1996 | Khwaja | 424/195.1 |
| 5,565,200 | 10/1996 | Khwaja | 424/195.1 |

OTHER PUBLICATIONS

Hayashi, *Folia Pharmacol Jpn* 73(2): 205–214 (1977). Abstract.*
Inagaki et al., *Nagoya Shiritsu Daigaku Yakugakubu Kenkyu Nempo* 15: 27–32 (1967). Abstract.*
Tang et al, "Chinese Drugs of Plant Origin", Chemistry, Pharmacology and Use in Traditional and Modern Medicine, pp. 613–619, Springer–Verlag (1992).
Honda et al, *Journal of Natural Products*, 51(1):152–154 (1988).
Tanaka et al, *Journal of Natural Products*, 49(3):466–469 (1986).
Tabata et al, *Journal of Medicinal Plant Research*, 44:234–236 (1982).
Kyoguku et al., *Syoyakugaku Zasshi*, 27(1):31–36 (1973).
Yuan et al, *Genetic Engineering News*, p. 14 (Apr. 15, 1997).
Yuan et al, "Herbal Medicines, Part I" and "Herbal Medicines—High Tech or Traditional", *Genetic Engineering News* (1996).
Lin et al, *Bio/Pharma Quarterly*, pp. 1–10 (Summer 1997).
Lin, *Journal of Food and Drug Analysis*, 5(4):235–240 (1997).
Woloshuk et al, *Herbalgram*, 37:18.
Tanaka et al, *Yakugaku Zasshi*, 95(5):525–530 (1972).
Lin et al, *Dokkyo J. of Medical Sciences*, 23(1):63–69 (1996).
Afzal et al, *Agric. Biol. Chem.*, 47(2):411–412 (1983).
Brigham et al, *Plant Physiology*, 114(3):223–224 (1997).
Meselhy et al, *Tetrahedron* 50(1):3081–3098 (1994).
Madigan et al, Brock Bilogy of Microorganisms, 8th ed., Prentice Hall, Upper Saddle Riber, NJ (1997).

* cited by examiner

*Primary Examiner*—Jean C. Witz
(74) *Attorney, Agent, or Firm*—Sughrue, Mion, Zinn, Macpeak & Seas, PLLC

(57) ABSTRACT

Compositions for treatment of antibiotic-resistant gram-positive bacterial infections, as well as methods for using and preparing the same, are disclosed.

20 Claims, 7 Drawing Sheets

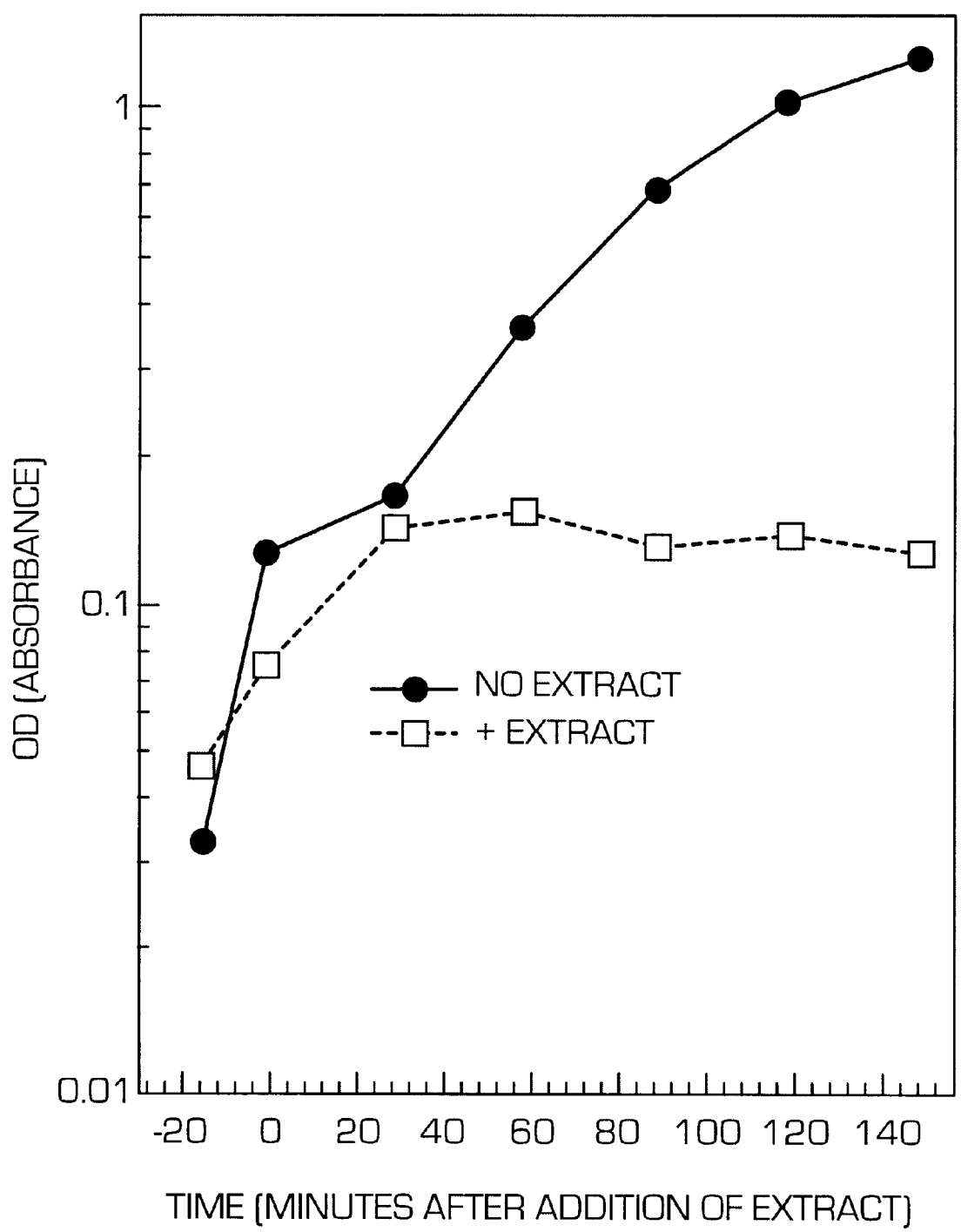

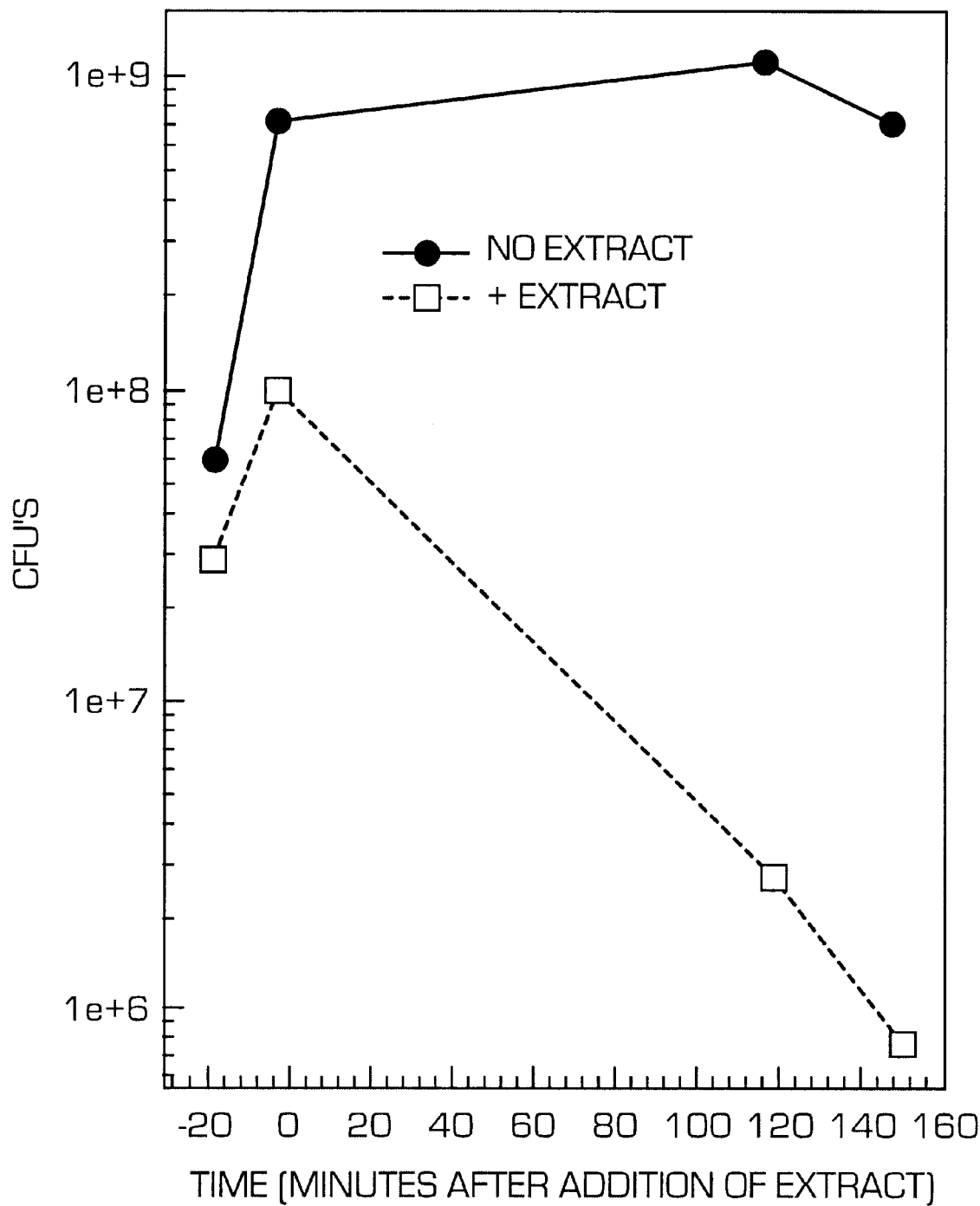

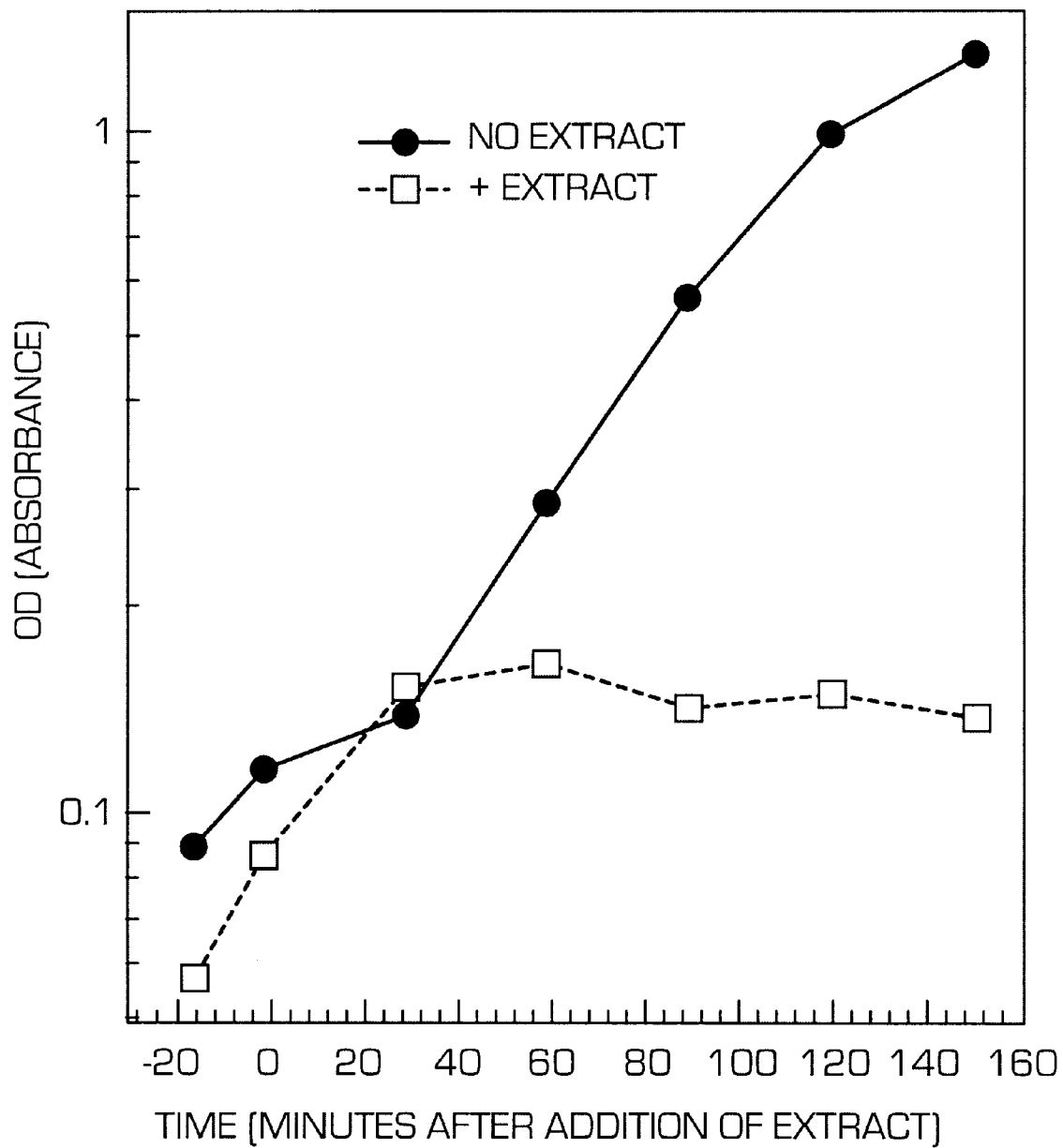

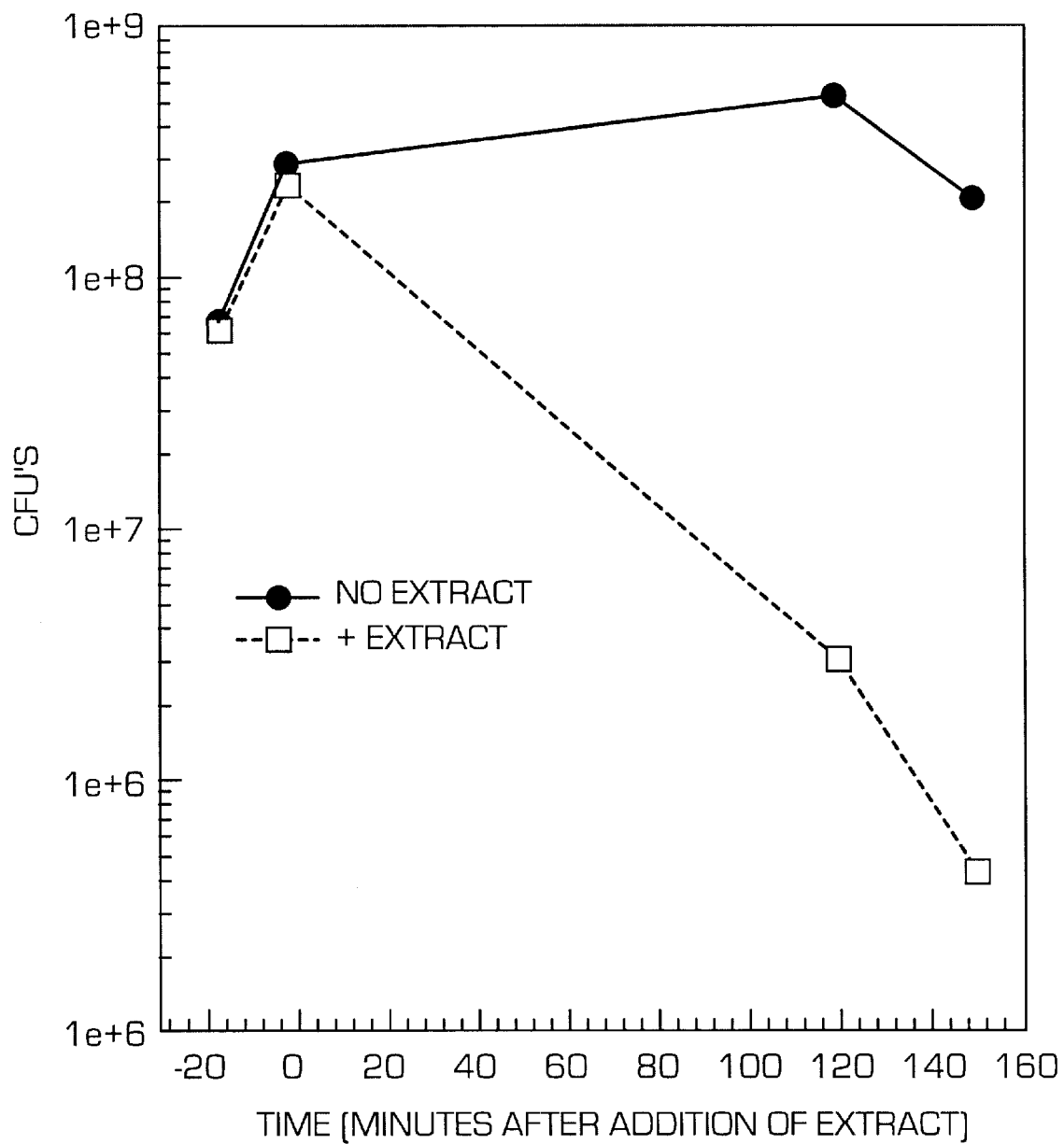

COMPOSITIONS FOR TREATMENT OF ANTIBIOTIC-RESISTANT GRAM-POSITIVE BACTERIAL INFECTIONS AND METHODS FOR USING AND PREPARING THE SAME

CROSS-REFERENCE TO RELATED APPLICATIONS

This is a Divisional of U.S. application Ser. No. 09/138,127, filed Aug. 24, 1998, U.S. Pat. No. 6,025,400.

FIELD OF THE INVENTION

The present invention relates to compositions for treatment of antibiotic-resistant gram-positive bacterial infections, as well as methods for using and preparing the same.

BACKGROUND OF THE INVENTION

I. Antibiotic Use and Antibiotic-Resistance

The term "antibiotic" is broadly defined as a chemical compound produced by one microorganism that inhibits the growth of a different microorganism. Today, there are more than 150 antibiotics which are classified by their chemical structures and mechanisms of action, examples of which are listed in Table 1 below (Lawson et al, *The American Biology Teacher*, 6:412–417 (1998)).

TABLE 1

Chemical Class and Mechanism of Action of Common Antibiotics

| Antibiotic | Class | Mechanism of Action |
|---|---|---|
| Ampicillin | Broad-spectrum penicillin | Inhibits cell wall synthesis |
| Ceftriaxone | 3rd generation cephalosporin | Inhibits cell wall synthesis |
| Erythromycin | Macrolide | Inhibit protein synthesis |
| Norfloxacin | Quinolone | Inhibits DNA synthesis |
| Streptomycin | Aminoglycoside | Inhibits protein synthesis |
| Sulfisoxazole | Sulfonamide | Competitive enzyme inhibitor |
| Tetracycline | Tetracycline | Inhibits protein synthesis |

When the first therapeutic antibiotic, penicillin, was introduced in the early 1940's, many believed that the threat from infectious diseases was over. However, in the past 25 years, through the abuse and misuse of antibiotics, many bacteria have developed resistance to these antibiotics. Today, there are strains of virtually every major bacterial human pathogen that are resistant to some of the most effective antibiotics. These strains include pathogens that can cause diarrhea, urinary tract infections, otitis media, meningitis, tuberculosis, gonorrhea, pneumonia, dysentery, wound infections, septicemia, bacteremia and surgical infections (Lippe, Breakout: The Evolving Threat of Drug-Resistant Diseases, Sierra Clubs, San Francisco (1995)).

Thus, while 90% of bacterial infections are successfully treated with first line antibiotics, there are increasingly situations in which over 40% of the infections are resistant to one or more antibiotics (including second line products). The newest antibiotic, vancomycin, has been shown to be the only antibiotic that is effective against some pathogenic bacteria. It has become the last line of defense against some infections, particularly those by methicillin-resistant *Staphylococcus aureus*.

In addition, some less pathogenic strains of the genus Enterococcus have vancomycin-resistance genes, and have been shown, in the laboratory, to transfer this resistance to Staphylococcus strains (Lawson et al, supra). As a result, the physician will have no treatment for infections by these Staphylococcus strains.

The mechanisms of bacterial resistance to antibiotics include the following:

(1) Loss of cell permeability to the antibiotic;

(2) Enzymes that render the antibiotic ineffective;

(3) Export of the antibiotic out of the cell once it enters the cell;

(4) Modification of the target of the antibiotic; and (5) Modification of metabolic pathways which result in by-passing the reaction inhibited by the antibiotic.

The seriousness of these mechanisms of antibiotic resistance is accentuated by the ability of the bacteria to transfer the resistance to other microorganisms, some of which may be fairly genetically unrelated to the antibiotic-resistant strain. The antibiotic-resistance transfer can occur through one of the following mechanisms: conjugation, transduction, transformation or transposition.

Antibiotic-resistant microorganisms add an estimated $200 million/year to medical bills. When costs for extended hospital stays are considered, the estimated costs increase by $30 billion/year (Phelps, Medical Care, 27:194–203 (1989)). Thus, there is a crucial need for novel antimicrobial agents which can effectively inhibit the growth of bacteria by mechanisms different from those of existing antibiotics.

II. Traditional Chinese Medical Herbal Formulations

The historic milestones in Traditional Chinese Medicine (TCM) are as follows:

3494 B.C.: The initial discovery of herbal medicine by emperor Shen Nong;

500 B.C.: The flowering of Chinese medicine: medicine, religion, ethics, philosophy; and 16th Century: Li Shizhen (1517–1593) writes Outlines and Divisions of Herbal Medicines.

The ancient Chinese understood the value of a combinatorial approach to the treatment of diseases. They believed that a disease can, and often, affects more than a single function and thus, treatment must be directed to multiple targets. A mixture of different herbs was thus, designed to neutralize the multiple effects of a disease. The Western "silver bullet" approach of one single chemical to cure one disease in all patients has not been readily accepted in TCM.

Most formulations of TCM contain 6 to 12 herbs. Throughout the history of TCM, there have been many different methods of classifying the ways in which medicinal substances can be combined (Liao Zhong-Chun, *Annotated Divine Husbandman's Classic of Materia Medica* (1625); and Bensky et al, *Chinese Herbal Medicine, Materia Medica*, Eastland Press, Seattle, Wash. (1993)). Formulations have been carefully crafted so as to accentuate and enhance functionality, to suppress and counteract toxicity, and to avoid antagonism and incompatibility. Since there are so many possible combinations from such a large collection of herbs, a hierarchical scheme has been developed. That is, the principal ingredient is a substance that provides the main therapeutic thrust, the second principal ingredient enhances or assists the therapeutic actions of the first, and the rest of the ingredients serve one or more of the following functions: treatment of accompanying symptoms, moderation of the harshness or toxicity of the primary substances, guidance of the medicine to the proper organs or exertion of a harmonizing effect.

III. Herbs with Antimicrobial Activities Described in the Chinese Pharmacopoeia

Many of the 5767 Chinese medicines (herbs, animals and minerals) listed in the *Encyclopedia of Traditional Chinese Medicinal Substances* (1977) have been used to combat microbial infections.

The herb Zi-Cao (literally translated as "Purple Herb"), is the dry root of *Lithospermum erythrorhizon* Sieb, et Zucc. or *Arnebia euchroma* (Royle) Johnst. These plants belong to the family Boraginaceae. This herb is officially listed in the Chinese Pharmacopoeia, and has frequently been used as an anti-inflammatory and anti-pyretic agent in the treatment of measles, eczema and thermal burns (Tang et al, *Chinese Drugs of Plant Origin*, pages 613–619, Springer-Verlag (1992)). The aqueous or organic extract of these roots has been used in combination with other herbs in the form of ointments for topical use, or in the form of aqueous infusions as an antipyretic to "cool the blood and as an antidote to body toxins induced by heat excess".

The roots of plants from the family of Boraginaceae contain naphthoquinone pigments as the main chemical constituents (Tang et al, supra). Shikonin and its derivatives are the main naphthoquinone pigments. Shikonin is a naphthoquinone with an unsaturated side chain and an asymmetric centrum bearing a hydroxy group. A series of carboxylic acid esters of shikonin have been identified (Morimoto et al, *Tetrahedron Lett.*, 52:4737–4739 (1965); Morimoto et al, *Tetrahedron Lett.*, 31:3677–3680 (1966); and Kyogoku et al, *Shoyakugagu Zasshi*, 27:24–30 (1973)). The chemical structures of shikonin and its identified derivatives are shown in FIG. 1.

The total organic solvent extract from root of a plant belonging to the family Boraginaceae, and some of the individual components of the extract, i.e., shikonin and deoxyshikonin, have been identified as having antimicrobial activity (Tanaka et al, *Yakugaku Zasshi*, 92:525–530 (1972); Kyogoku et al, *Shoyakugaku Zasshi*, 27:31–36 (1973); and Honda et al, *J. Natural Products*, 51:152–154 (1988)); and anti-inflammatory activity (Tanaka et al, *J. Natural Products*, 9:466–469 (1986)). However, there is no teaching or suggestion in the art that the extracts, or components thereof, are effective against antibiotic-resistant bacteria, much less gram-positive antibiotic-resistant bacteria.

SUMMARY OF THE INVENTION

An object of the present invention is to provide antimicrobial agents which can effectively inhibit the growth of bacteria by mechanisms different from those of existing antibiotics.

Still another object of the present invention is to provide compositions which are useful for treatment of antibiotic-resistant gram-positive bacterial infections.

Yet another object of the present invention is to provide methods for treatment of antibiotic-resistant gram-positive bacterial infections.

An additional object of the present invention is to provide methods for obtaining said compositions.

These and other objects of the present invention, which will be apparent from the detailed description of the invention provided hereinafter, have been met, in one embodiment by a method for the treatment of antibiotic-resistant gram-positive bacterial infections comprising administering to a subject infected with antibiotic-resistant gram-positive bacteria, a pharmaceutically effective amount of a total organic solvent extract from root of Boraginaceae.

BRIEF DESCRIPTION OF THE DRAWINGS

FIGS. 4A–4B show growth curves of a wild-type strain of *Staphylococcus aureus* (ATCC 29213) in the presence and absence of a total organic solvent extract from *Arnebia euchroma*. FIG. 4A is plotted as OD vs. time; and FIG. 4B is plotted as CFU vs. time.

FIGS. 5A–5B show growth curves of an antibiotic-resistant strain of *Staphylococcus aureus* (ATCC 27695) in the presence and absence of a total organic solvent extract from *Arnebia euchroma*. FIG. 5A is plotted as OD vs. time; and FIG. 5B is plotted as CFU vs. time.

DETAIL DESCRIPTION OF THE INVENTION

Figure 1:
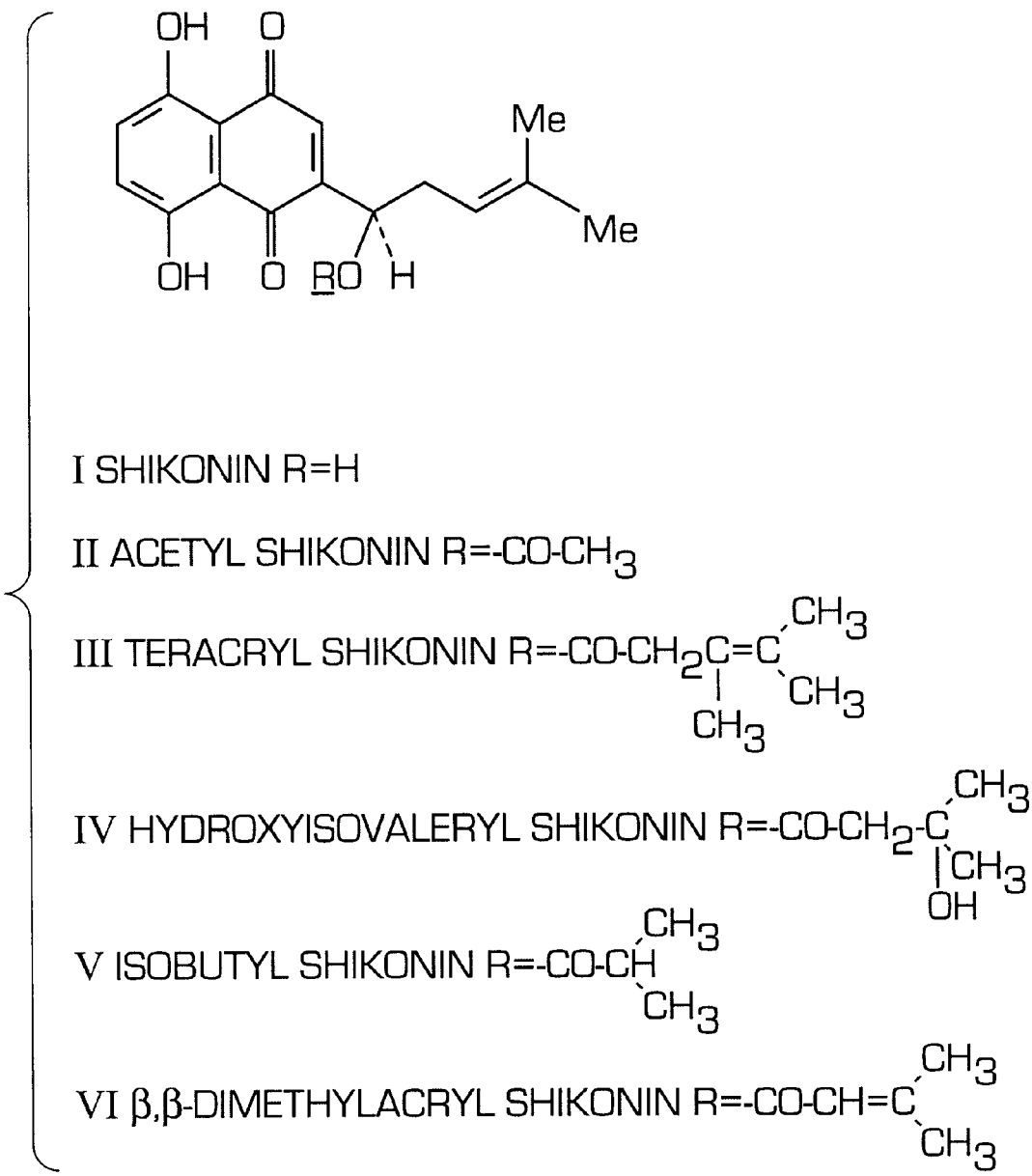
FIG. 1 shows the chemical structures of the major active ingredients found in the root of *Arnebia euchroma* and *Lithospermum erythrorhizon*.

As discussed above, in one embodiment, the present invention relates to a method for the treatment of antibiotic-resistant gram-positive bacterial infections comprising administering to a subject infected with antibiotic-resistant gram-positive bacteria, a pharmaceutically effective amount of a total organic solvent extract from root of Boraginaceae.

As used herein "total organic solvent extract" means the total solid material obtained by extracting the dry roots of herbs with an organic solvent.

The organic solvent used to obtain the extract is not critical to the present invention. Examples of such organic solvents include sesame seed oil, methanol, ethanol, chloroform, and ether. Sesame seed oil and methanol are the preferred organic solvents used to obtain the extracts.

Plants of the Boraginaceae family whose root is employed is not critical to the present invention. Examples of such plants include *Arnebia euchroma, Lithospermum erythrorhizon*, and *Arnebia guttata*. *Arnebia euchroma* is the preferred plant used in the present invention.

The ratio of root to solvent used to prepare the extract is generally about 1:20 to 1:5 (w/v), preferably about 1:10 (w/v).

It is preferable when preparing the extract to minimize exposure to light, and high temperatures, e.g., temperatures above 50° C. should be avoided.

The total organic solvent extract of the present invention generally comprises from about 0.05–0.25% (w/w) shikonin, from about 1.8–2.8% (w/w) acetyl shikonin, from about 0–0.8% (w/w) teracyl shikonin, from about 0.15–1.5% (w/w) hydroxyisovaleryl shikonin, from about 2.0–6.5% (w/w) isobutyl shikonin, and from about 1.5–4.5% (w/w) β,β-dimethylacryl shikonin. Preferably, the total organic solvent extract of the present invention comprises from about 0.1–0.2% (w/w) shikonin, from about 2.0–2.5% (w/w) acetyl shikonin, from about 0.05–0.5% (w/w) teracyl shikonin, from about 0.2–1.0% (w/w) hydroxyisovaleryl shikonin, from about 2.5–5.5% (w/w) isobutyl shikonin, and from about 2.5–4.0% (w/w) β,β-dimethylacryl shikonin.

In another embodiment, the present invention relates to a method for the treatment of antibiotic-resistant gram-positive bacterial infections comprising administering to a subject infected with antibiotic-resistant gram-positive bacteria, a pharmaceutically effective amount of a red colored active fraction of a total organic solvent extract from root of Boraginaceae.

As used herein "red colored active fraction of a total organic solvent extract" means the red colored fraction of the total organic solvent extract obtained by thin layer chromatography (TLC) or a silica gel column and chloroform as the developing solvent. The major components in this red colored fraction are naphthoquinones, and thus the fraction can also be referred to as the "naphthoquinone fraction".

The red colored active fraction of the present invention generally comprises from about 0.5–2.5% (w/w) shikonin, from about 18–28% (w/v) acetyl shikonin, from about 0–8.0% (w/w) teracyl shikonin, from about 1.5–15% (w/w) hydroxyisovaleryl shikonin, from about 20–65% (w/w) isobutyl shikonin, and from about 15–45% (w/w) β,β-dimethylacryl shikonin. Preferably, the red colored active fraction of the present invention comprises from about 1.0–2.0% (w/w) shikonin, from about 20–25% (w/w) acetyl shikonin, from about 0.5–5.0% (w/w) teracyl shikonin, from about 2.0–10% (w/w) hydroxyisovaleryl shikonin, from about 25–55% (w/w) isobutyl shikonin, and from about 25–40% (w/w) β,β-dimethylacryl shikonin.

In still another embodiment, the present invention relates to a method for the treatment of antibiotic-resistant gram-positive bacterial infections comprising administering to a subject infected with antibiotic-resistant gram-positive bacteria, a pharmaceutically effective amount of a composition comprising acetyl shikonin and β,β-dimethylacryl shikonin.

In the composition of the present invention acetyl shikonin and β,β-dimethylacryl shikonin are each generally present in an amount of from about 20–60% (w/w), preferably about 25–40% (w/w). Other naphthoquinone compounds may also be present.

As defined herein "antibiotic-resistant" gram-positive bacteria are those whose growth cannot be inhibited by commonly used antibiotics, e.g., those listed in Table 1 above. The particular antibiotic-resistant gram-positive bacteria whose growth are inhibited by the treatment of the present invention is not critical thereto. Examples of such antibiotic-resistant gram-positive bacteria include antibiotic-resistant *Staphylococcus aureus, Enterococcus faecalis,* and *Streptococcus pneumoniae.*

The particular mode of administration is not critical to the present invention. For example, the total organic solvent extract, red colored fraction or composition can be administered topically or orally. Topical use is the preferred mode of administration.

The particular pharmaceutically effective amount of the total organic solvent extract employed in the present invention is not critical thereto. The particular amount to be administered in accordance with the present invention varies depending upon the mode of administration, the bacteria to be treated, the severity or extent of infection, whether administered alone or in combination with other drugs, and the age, weight and sex of the subject to be treated. Generally, the amount to be administered topically is in the range of about 0.5 to 20 mg/cm$^2$, preferably about 2.0 to 5.0 mg/cm$^2$. Generally, the amount to be administered orally is in the range of about 1.0 to 75 mg/dose, preferably about 10 to 25 mg/dose.

The particular pharmaceutically effective amount of the red colored active fraction employed in the present invention is not critical, thereto. The particular amount to be administered in accordance with the present invention varies depending upon the mode of administration, the bacteria to be treated, the severity or extent of infection, whether administered alone or in combination with other drugs, and the age, weight and sex of the subject to be treated. Generally, the amount to be administered topically is in the range of about 0.05 to 2.0 mg/cm$^2$, preferably about 0.2 to 0.5 mg/cm$^2$. Generally, the amount to be administered orally is in the range of about 0.1 to 7.5 mg/dose, preferably about 1.0 to 2.5 mg/dose.

The particular pharmaceutically effective amount of the composition employed in the present invention is not critical thereto. The particular amount to be administered in accordance with the present invention varies depending upon the mode of administration, the bacteria to be treated, the severity or extent of infection, whether administered alone or in combination with other drugs, and the age, weight and sex of the subject to be treated, as well as the concentration of acetyl shikonin and β,β-dimethylacryl shikonin in the composition. Generally, the amount to be administered topically is in the range of about 0.03 to 1.0 mg/cm$^2$, preferably about 0.1 to 0.4 mg/cm$^2$. Generally, the amount to be administered orally is in the range of about 0.05 to 4.0 mg/dose, preferably about 0.5 to 1.5 mg/dose.

The total organic solvent extract or red colored active fraction thereof or composition of the present invention can be used alone, or in combination with other herbs, e.g., borneol, *Radix agnelicae sinensis, Flos carthami tinctorii,* and *Radix glycyrrhizae* (Hu, *Handbook of Clinical Applications of Chinese Herbal Medicines,* Beijing (1993)).

Furthermore, the total organic solvent extract or red colored active fraction thereof or composition of the present invention can be used, e.g., in the form of an ointment, a solution or as a cream. The total organic solvent extract or red colored active fraction thereof or composition can be admixed with any conventional oil, wax petroleum jelly and other inert excipients to obtain ointments and creams; or with conventional organic solvents (e.g., methanol, ethanol or isopropanol) to obtain solutions.

The following Examples are provided for illustrative purposes only, and are in no way intended to limit the scope of the present invention.

EXAMPLE 1

Preparation of Total Organic Solvent Extract

Dry roots of each of *Arnebia euchroma* and *Lithospermum erythrorhizon* were soaked overnight at room temperature (22–27° C.) in an organic solvent, e.g., methanol or ethanol, at a ratio of 1 part dry root:10 parts solvent (w/v). The resulting mixture was then filtered through a Whatman #1 filter to remove the solid material. The volume of the filtrate was reduced to 1/10 of its original volume by evaporation, and acidified by the addition of 1/10 volume of 2.0 N HCl (or any other inorganic acid). The resulting red precipitate was collected by centrifugation at 26,000×g, and air dried. The resulting sticky residue, i.e., the "total organic solvent extract", was used in the anti-bacterial assays described in Example 4 below.

EXAMPLE 2

Partial Fractionation of Total Organic Solvent Extract

An active fraction, i.e., the red colored active fraction, of the total organic solvent extracts was obtained using thin layer chromatography (TLC) or a silica gel column, as described in detail below.

A. Thin Layer Chromatography

The total organic solvent extract from *A. euchroma,* obtained as described in Example 1 above, was dissolved in a minimal amount (approximately 1:10 (w/v)) of chloroform, and then applied as a band at the bottom of a 20×20 cm silica gel plate (Sigma Chemical Co.). The plate was then developed in chloroform at room temperature (22–27° C.) until the solvent reached the top of the plate. All of the observed red bands were scraped from the plate and combined. Then, a red colored active fraction was obtained by packing the silica mix in a glass column and eluting it with chloroform.

B. Silica Gel Column

Silica gel was packed into a glass column using chloroform as the solvent. The total organic solvent extract from *A. euchroma*, obtained as described in Example 1 above, was dissolved in a minimal amount (approximately 1:10 (w/v)) of chloroform, and then layered onto the top of the column. Then, a red colored active fraction was obtained by slowly eluting it from the column with chloroform.

EXAMPLE 3

Figure 2:
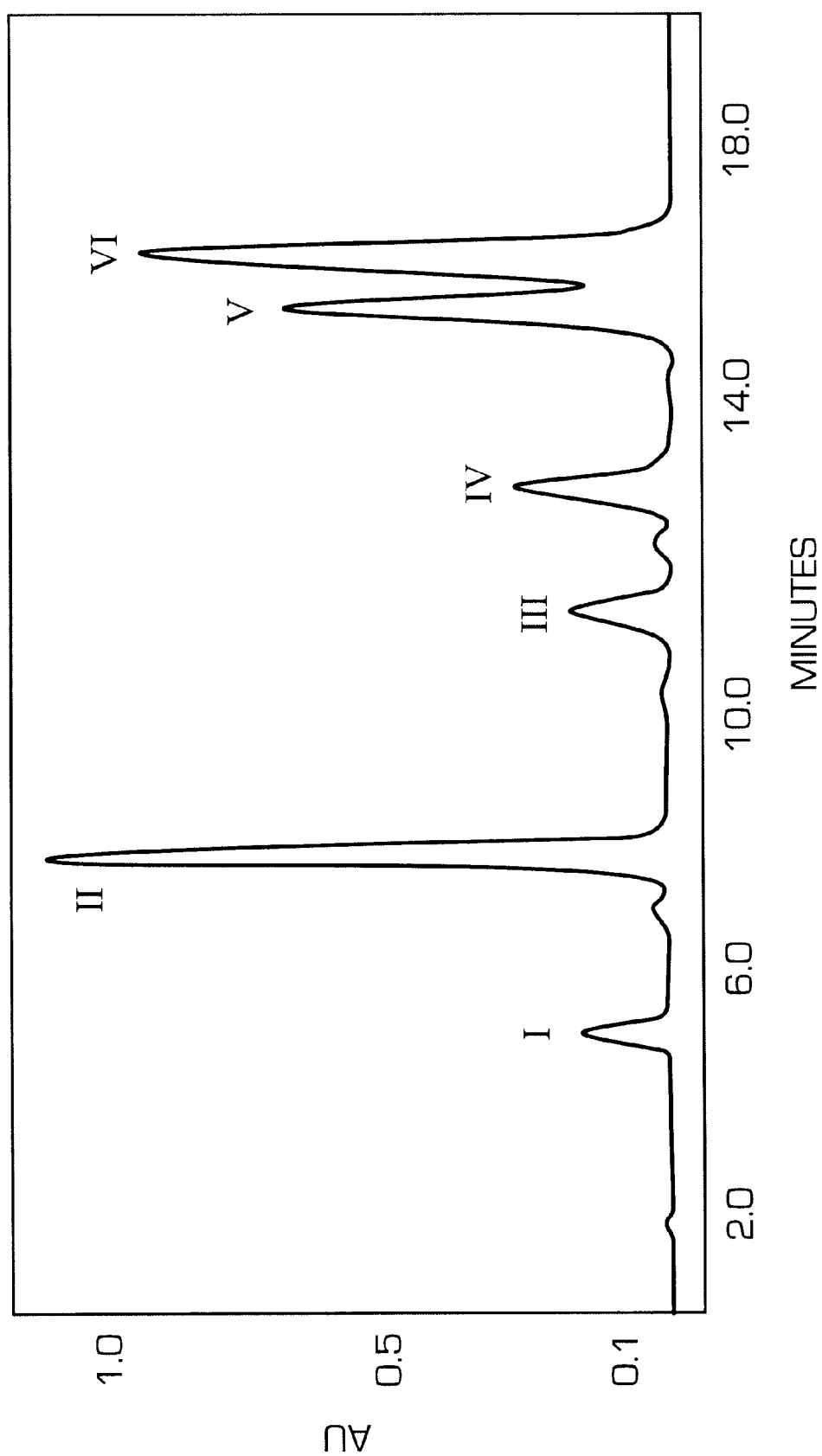
FIG. 2 is an HPLC chromatogram of a total organic solvent extract from *Arnebia euchroma*.
Figure 3:
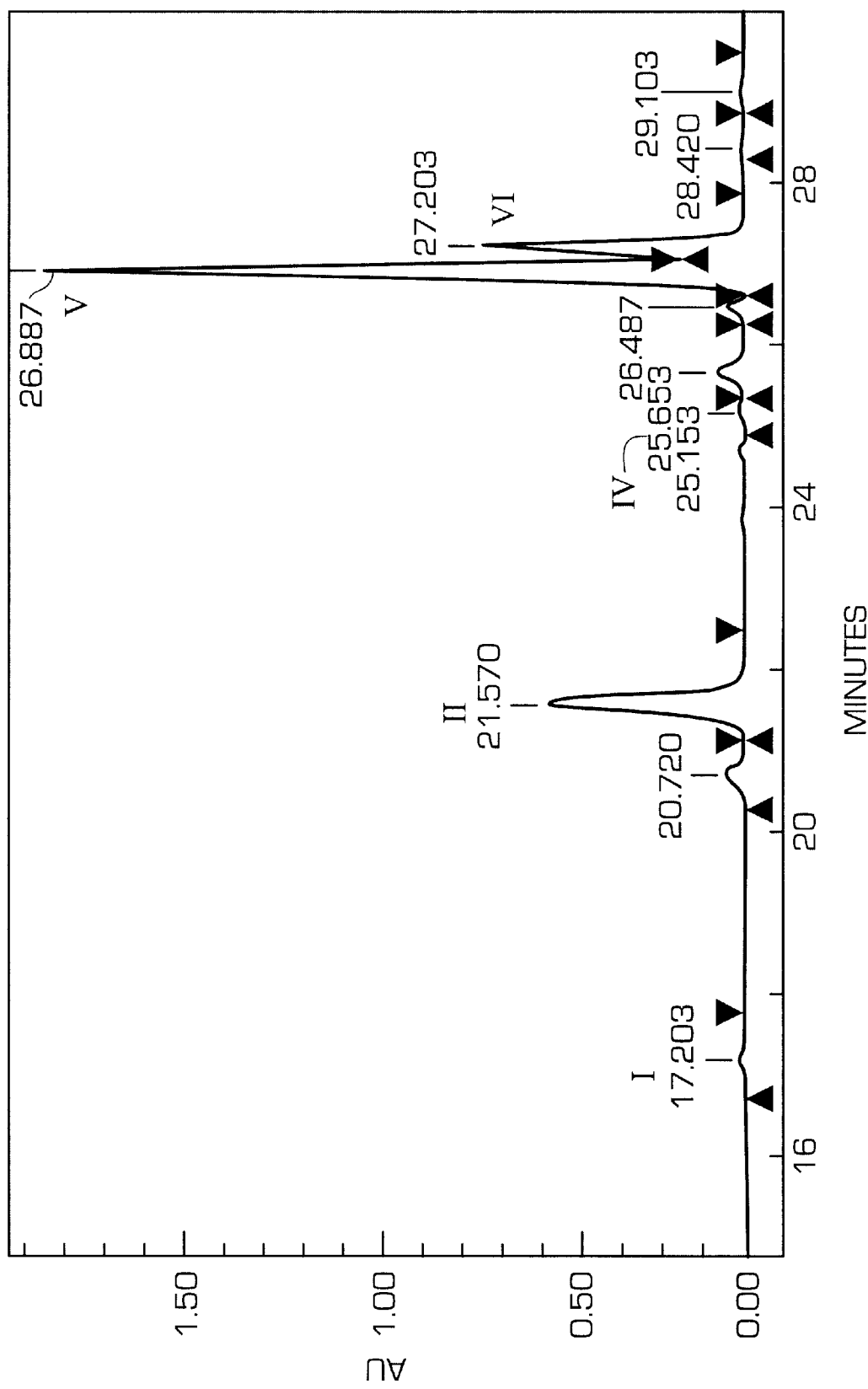
FIG. 3 is an HPLC chromatogram of a total organic solvent extract from *Lithospermum erythrorhizon*.

Composition of Shikonin and Its Derivatives in the Total Organic Solvent Extract The content of shikonin and its derivatives varies with the plant species, and the location where the plant is collected. FIGS. 2 and 3 represent the High Performance Liquid Chromatography (HPLC) patterns of total organic solvent extracts from representative batches of *Arnebia euchroma* and *Lithospermum erythrorhizon*, respectively. The HPLC was performed by a reverse phase C-18 column using a linear gradient of 18 to 90% (v/v) acetonitrile in the presence of 2.0% (v/v) acetic acid.

The average content of total naphthaquinone pigments in the total organic solvent extracts obtained in Example 1 above were calculated from the optical density coefficient and found to be 6.0% to 10% (w/w). The average content of total naphthaquinone pigments in the red colored active fraction obtained in Example 2 above were also calculated from the optical density coefficient and found to be >95% (w/w). The percentage of each component in a typical batch of the red colored active fraction was calculated by comparing with standards of known weight. The results are shown in Table 2 below.

TABLE 2

Composition of Shikonin and Its Derivatives in the Red Colored Active Fraction

| | Peak | % (w/w) in A. euchroma | % (w/w) in L. erythrorhizon |
|---|---|---|---|
| I. | Shikonin | 2.0 | 0.8 |
| II. | Acetyl shikonin | 24.0 | 20.1 |
| III. | Teracryl shikonin | 4.5 | trace |
| IV. | Hydroxyisovaleryl shikonin | 9.0 | 2.9 |
| V. | Isobutyl shikonin | 26.0 | 55.9 |
| VI. | β, β-dimethylacryl shikonin | 34.5 | 20.3 |

EXAMPLE 4

Antimicrobial Activity

The antimicrobial activities of the total organic solvent extract from *A. euchroma*, obtained as described in Example 1 above, and the red colored active fraction from *A. euchroma*, obtained as described in Example 2 above, were evaluated using a disk sensitivity assay.

More specifically, wild-type *Staphylococcus aureus* (ATCC 29212) was grown in Luria broth (L-broth) at 37° C. to exponential phase, diluted to $1.0 \times 10^7$ bacteria/ml, and mixed with minimal medium (M63, +salt and glucose) with 0.15% (w/v) soft agar. The mixture was poured over a minimal agar plate (minimal medium +0.7% (w/v) agar). Filter paper disks (6.0 mm in diameter) were then impregnated with 20 µl of total organic solvent extract from *A. euchroma* (containing 10 mg/ml of naphthaquinone compounds in dimethyl formamide (DMF)); 20 µl of total organic solvent extract from *L. erythrorhizon* (containing 10 mg/ml of naphthaquinone compounds in DMF); 20 µl of the red colored active fraction from *A. euchroma* isolated using TLC (10 mg/ml in DMF); 20 µl of the red colored active fraction from *A. euchroma* isolated using the silica gel column (10 mg/ml in DMF); or 20 µl of DMF as control, and placed on the surface of the agar plates. The plates were then incubated at 37° C. for 18 hrs. In this assay, clear zones surrounding the disks indicated that there was inhibition of bacterial growth by the material diffusing from the filter paper disks. The results are shown in Table 3 below.

TABLE 3

Antimicrobial Activities of Total Organic Solvent Extracts and Red Colored Active Fractions Against Wild-Type *S. aureus*

| Test sample | Zone of Inhibition (mm) |
|---|---|
| Total extract of *A. euchroma* | 9.0 |
| Total extract of *L. erythrorhizon* | 8.5 |
| TLC isolated fraction | 9.0 |
| Silica gel isolated fraction | 8.5 |
| Control | 0.0 |

As shown in Table 3 above, all of the samples were found to be active against the test organism.

A. Total Organic Solvent Extract

1. Activity on Gram-Positive and Gram-Negative Bacteria

The disk assay described above was next carried out using the total organic solvent extract from *A. euchroma*, obtained as described in Example 1 above, and various gram-positive or gram-negative antibiotic-sensitive bacteria. The results are shown in Table 4 below.

TABLE 4

Activity of Total Organic Solvent Extract on Antibiotic-Sensitive Bacteria

| Bacteria strain | Gram +/− | Inhibitory effect |
|---|---|---|
| *Staphylococcus aureus* | + | Yes |
| *Streptococcus pyrogenes* | + | Yes |
| *Streptococcus epidermis* | + | Yes |
| *Enterococcus faecalis* | + | Yes |
| *Protens vulgaris* | + | No |
| *E. coli* K12 | − | No |
| *E. coli* IMP4213* | − | Yes |

*a hyper-permeable *E. coli* strain

As shown in Table 4 above, the total organic solvent extract exhibited growth inhibitory activity against almost all the gram-positive bacteria, but not against gram-negative bacteria, unless the latter was rendered hyper-permeable prior to the addition of the extract.

2. Activity on Antibiotic-Resistant Bacteria and Clinical Isolates

The disk assay described above was carried out using antibiotic-resistant *Staphylococcus aureus* (ATCC 27695), and 20 μl of the total organic solvent extract from *A. euchroma* (containing 10 mg/ml of naphthaquinone compounds in DMF); 20 μl of the total organic solvent extract from *L. erythrorhizon* (containing 10 mg/ml of naphthaquinone compounds in DMF); or 20 μl of DMF as a control. The results are shown in Table 5 below.

TABLE 5

Antimicrobial Activities of Total Organic Solvent Extracts and Red Colored Active Fractions Against Antibiotic-Resistant *S. aureus*

| Test sample | Zone of Inhibition (mm) |
|---|---|
| Total extract from *A. euchroma* | 9.5 |
| Total extract from *L. erythrorhizon* | 9.0 |
| TLC isolated fraction | 9.0 |
| Silica gel isolated fraction | 9.0 |
| Control | 0.0 |

As shown in Table 5 above, all of the samples exhibited growth inhibitory activity against the antibiotic-resistant *S. aureus*.

Next, another disk assay was carried out as described above using the total organic solvent extract from *A. euchroma*, obtained as described in Example 1 above, and strains of antibiotic-resistant *Staphylococcus aureus*, which were obtained as clinical isolates from a hospital in Beijing. The results are shown in Table 6 below.

TABLE 6

Activity of Total Organic Solvent Extract on Antibiotic-Resistant *S. aureus*

| Strain | Antibiotic Resistance (MIC* μg/ml) | Zone of inhibition (mm) |
|---|---|---|
| 6515 | Penicillin G (>20) | 10.87 |
| 1206 | Tetracycline (>32) | 12.18 |
| 3-44 | Tetracycline, Erythromycin (>32) | 12.56 |
| 5-75 | Erythromycin (>32) | 12.17 |
| 5-76 | Erythromycin (>32) | 12.63 |
| 5-77 | Erythromycin (>32) | 11.35 |
| 5-78 | Erythromycin (4) | 12.05 |
| 4-44 | Piperacillin (>128) | 12.24 |
| 3-16 | Methicillin, Piperacillin (32) | 12.22 |
| 3-20 | Methicillin, Piperacillin (128) | 11.68 |
| 5-37 | Methicillin, Piperacillin (>128) | 0.00 |
| 5-38 | Methicillin, Piperacillin (32) | 13.69 |
| 5-39 | Methicillin, Piperacillin (128) | 12.60 |
| 5-47 | Methicillin, Piperacillin (>128) | 13.02 |
| 4-15 | Piperacillin (32) | 12.67 |
| 4-50 | Piperacillin (32) | 12.42 |

*MIC: Minimum Inhibition Concentration

As shown in Table 6 above, the total organic solvent extract exhibited growth inhibition on 15 out of 16 *S. aureus* clinical isolates from a hospital in Beijing where almost all *S. aureus* infections are resistant to antibiotic treatment.

As shown in Tables 3 to 6 above, the total organic solvent extract from the Chinese herb, *A. euchroma*, is effective in inhibiting the growth of a broad spectrum of gram-positive bacteria, including those resistant to antibiotics.

3. Minimum Inhibitory Concentration (MIC)

Next, the MIC for the total organic solvent extract from *A. euchroma*, obtained as described in Example 1 above, against wild-type *Staphylococcus aureus* and antibiotic-resistant *Staphylococcus aureus* were determined in liquid culture using L-broth with different amounts of total organic solvent extract, and compared to the MIC for common antibiotics.

More specifically, different concentrations of total organic solvent extract was added to 1.0 ml of L-broth, and inoculated with 50 μl of an overnight growth of bacteria (about $1.0 \times 10^8$ cells). The resulting samples were incubated overnight at 37° C. The MIC was then determined by measuring the minimal concentration of extract needed to inhibit the growth of the bacteria. The results are shown in Table 7 below.

TABLE 7

Minimum Inhibitory Concentrations

| | (MIC μg/ml) | |
|---|---|---|
| Extract or Antibiotic | Wild-Type Strain | Antibiotic-Resistant Strain |
| Total organic solvent extract | 0.5–1.0 | 0.5–1.0 |
| Tetracycline | 1.0–2.0 | >20 |
| Erythromycin | 0.0–1.0 | >20 |
| Novobiocin | 0.0–2.0 | >20 |

As shown in Table 7 above, the total organic solvent extract from *A. euchroma* inhibited the growth of wild-type bacteria at a minimum concentration similar to the MIC for the antibiotics used. The same extract inhibited the growth of antibiotic-resistant bacteria at the same MIC as for the wild-type bacteria, while the antibiotic-resistant strain showed resistance to all three of the antibiotics tested.

4. Growth Inhibition in the Presence or Absence of the Total Organic Solvent Extract To determine whether the total organic solvent extract from *A. euchroma* acts in a bactericidal or bacteriostatic manner, growth curves were determined.

More specifically, wild-type *S. aureus* (ATCC 29213) and antibiotic-resistant *S. aureus* (ATCC 27659) were each grown to exponential phase in L-broth at 37° C., and 2.0 μg/ml of the total organic solvent extract was added thereto. The optical density (OD) at 600 nm, and the colony forming units (CFU) were then determined at different time intervals. For the control, only solvent, i.e., DMF, was added to the bacteria. The results are shown in FIGS. 4A–4B and FIGS. 5A–5B, respectively.

As shown in both FIG. 4A (wild-type *S. aureus*) and FIG. 5A (antibiotic-resistant *S. aureus*), 30 min after the addition of the total organic solvent extract, the total OD, which measures all of the bacterial particles, i.e., live or dead bacteria, ceased to increase, whereas for the control, the OD continued to increase. Further, as shown in both FIG. 4B (wild-type *S. aureus*) and FIG. 5B (antibiotic-resistant *S. aureus*), 30 min after the addition of the total organic solvent extract, viable cells, measured by their ability to form colonies, decreased rapidly.

The organic solvent extract killed >99% of the microorganisms tested. However, the minute population of surviving bacteria are sensitive to the total organic solvent extract when regrown in fresh media. Thus, it is likely that the minute population of bacteria that was initially resistant to inhibition by the total organic solvent extract was at a metabolic stage that rendered the bacteria insensitive to the total organic solvent extract. Upon re-culturing, these cells re-entered a new growth cycle, and again become sensitive to the total organic solvent extract.

5. Absence of Resistant-Mutant Bacteria

Using conditions that are similar to those commonly used for production of antibiotic mutants, attempts were made to obtain mutants resistant to the total organic solvent extract.

More specifically, the total organic extract from *A. euchroma*, obtained as described Example 1 above, was mixed with 0.15% (w/v) of agar, and added to the top of a M63 plate. Then, 1.0 ml of different strains of overnight growth of antibiotic-resistant *S. aureus* were added, and incubated at 37° C. overnight. Under similar conditions, a single antibiotic will generate antibiotic-resistant mutants. However, attempts to generate mutants resistant to the total organic solvent extract were unsuccessful.

These results demonstrate that either the target of the total organic solvent extract for the microorganism is essential and any mutation in the target is lethal, or that the total organic solvent extract affects different targets, making it very difficult for the bacteria to overcome the multiple hits simultaneously.

B. Red Colored Active Fraction

1. Activity on Gram-Positive and Gram-Negative Bacteria

The disk assay described above was used on the gram-positive and gram-negative bacteria shown in Table 4 above using 20 μl of the red colored active fraction from *A. euchroma* isolated using TLC (10 mg/ml in DMF); 20 μl of the red colored active fraction from *A. euchroma* isolated using the silica gel column (10 mg/ml in DMF); or 20 μl of DMF as control.

The anti-microbial activities of the red colored active fractions parallelled those for the total organic solvent extract. That is, the red colored active fractions were active against gram-positive bacteria, but not against gram-negative bacteria, except when the latter were rendered hyper-permeable by genetic manipulation.

2. Activity on Antibiotic-Resistant Bacterial Isolates

The disk assay described above was carried out on wild-type *S. aureus* and antibiotic-resistant *S. aureus* using 20 μl of the red colored active fraction from *A. euchroma* isolated using TLC (10 mg/ml in DMF); 20 μl of the red colored active fraction from *A. euchroma* isolated using the silica gel column (10 mg/ml in DMF); or 20 μl of DMF as a control. The results are shown in Tables 3 and 5 above.

As shown in Tables 3 and 5 above, the activities of the red colored active fractions against both the wild-type *S. aureus* (Table 3) and antibiotic-resistant *S. aureus* (Table 5) were found to be similar to that for the total organic solvent extracts.

3. Minimum Inhibition Concentration

The MIC of the red colored active fraction from *A. euchroma* were determined using *S. aureus*, and the liquid culture method as described above. The results are shown in Table 8 below.

TABLE 8

MIC at the Total Organic Solvent Extract and Red Colored Active Fractions

| Extract or Fraction | MIC (μg/ml) |
|---|---|
| Total organic solvent extract | 0.5–1.0 |
| Active Fraction obtained | |
| by TLC | 1.0–2.0 |
| by Silica gel | 1.0–2.0 |

As shown in Table 8 above, while active, the red colored active fractions were somewhat less potent in inhibiting the growth of bacteria than the total organic solvent extract.

C. Individual Components of Red Colored Active Fraction

Individual components were isolated from the red colored active fraction by preparative TLC and HPLC.

More specifically, the total organic solvent extract was dissolved in chloroform (1:10 (w/v)) and streaked at the bottom of the TLC plate, which was developed in chloroform. The six individual red colored bands were scraped from the plate, and the pigments were separated from the silica gel by eluting with chloroform. Those bands which were too close together were separated by HPLC using the same conditions described in Example 3 above.

1. Activity on Wild-type and Antibiotic Resistant Strains of *S. aureus*

The anti-microbial activities of the 6 individual components were determined using the disk sensitivity assay described above.

More specifically, filter paper disks impregnated with 20 μl of each individual component (2.0 mg/ml) were placed on top of the agar plate. The plates were developed as described in Example 4 above. The results are shown in Table 9 below.

TABLE 9

Inhibitory Activities of Individual Components

| | Zone of inhibition (mm) | |
|---|---|---|
| Component | Wild-Type Strain | Antibiotic-resistant Strain |
| Peak I | 18 | 18 |
| Peak II | 10 | 17 |
| Peak III | 7.5 | 7.0 |
| Peak IV | 7.0 | 7.0 |
| Peak V | 7.0 | 7.0 |
| Peak VI | 7.0 | 7.0 |

As shown in Table 9 above, each of the 6 individual components inhibited the growth of both wild-type *S. aureus* and antibiotic-resistant *S. aureus*. However, the sizes of the zones of inhibition were different, indicating different rate of diffusion and different inhibitory activities. That is, shikonin (Peak I), gave a large zone of inhibition, but the inhibition was not complete, as shown by an opaque, rather than a clear zone. Other components gave smaller, but clear zones of inhibition.

2. Minimum Inhibition Concentration

The MIC of the six individual components were determined using wild-type *S. aureus* and the liquid culture method as described above. The results are shown in Table 10 below.

TABLE 10

MIC of the Total Organic Solvent Extract, Red Colored Active Fraction and Individual Components

| Extract or component | MIC (µg/ml) |
| --- | --- |
| Total alcoholic extract | 0.5–1.0 |
| Fraction obtained by | |
| by TLC | 1.0–2.0 |
| by Silica gel | 1.0–2.0 |
| Peak I | 4.0–5.0 |
| Peak II | 0.5–1.0 |
| Peak III | 4.0–6.0 |
| Peak IV | 4.0–6.0 |
| Peak V | 2.0–4.0 |
| Peak VI | 0.0–2.0 |

As shown in Table 10 above, among the individual components, Peak II (acetyl shikonin) and Peak VI (β,β-dimethylacryl shikonin) were the most active. These two components are also the most prominent peaks which make up a total of 60% of the total naphthoquinone pigments in the red colored fraction.

3. Single Component vs. Mixture

From the data presented above, it is evident that the total organic solvent extract is the most active preparation for bactericidal activity. The red colored active fractions had slightly less activity, but are believed to have better toxicity profiles. Some individual components showed comparable antibacterial activity to the mixture found in the total organic solvent extract or the red colored active fractions. A mixture of the individual components is believed to provide a better therapeutic value, since it makes it almost impossible for the bacteria to develop resistance thereto.

While the invention has been described in detail, and with reference to specific embodiments thereof, it will be apparent to one of ordinary skill in the art that various changes and modifications can be made therein without departing from the spirit and scope thereof.

What is claimed:

1. A method for the treatment of antibiotic-resistant gram-positive bacterial infections comprising administering to a subject infected with antibiotic-resistant gram-positive bacteria, a pharmaceutically effective amount of a total organic solvent extract from root of Boraginaceae.

2. The method of claim 1, wherein said antibiotic-resistant gram-positive bacteria are selected from the group consisting of antibiotic-resistant *Staphylococcus aureus*, antibiotic-resistant *Enterococcus faecalis*, and antibiotic-resistant *Streptococcus pneumoniae*.

3. The method of claim 1, wherein said extract is administered by a mode selected from the group consisting of topical administration and oral administration.

4. The method of claim 3, wherein said pharmaceutically effective amount is about 0.5 to 20 mg/cm$^2$ administered topically, and about 1.0 to 75 mg/dose administered orally.

5. The method of claim 4, wherein said pharmaceutically effective amount is about 2.0 to 5.0 mg/cm$^2$ administered topically, and about 10 to 25 mg/dose administered orally.

6. The method of claim 1, wherein said Boraginaceae is a member selected from the group consisting of *Arnebia euchroma*, *Lithospermum erythrorhizon* and *Arnebia guttata*.

7. The method of claim 1, wherein said total organic solvent extract comprises from about 0.05–0.25% (w/w) shikonin, from about 1.8–2.8% (w/w) acetyl shikonin, from about 0–0.8% (w/w) teracyl shikonin, from about 0.15–1.5% (w/w) hydroxyisovaleryl shikonin, from about 2.0–6.5% (w/w) isobutyl shikonin, and from about 1.5–4.5% (w/w) β,β-dimethylacryl shikonin.

8. The method of claim 7, wherein said total organic solvent extract comprises from about 0.1–0.2% (w/w) shikonin, 2.0–2.5% (w/w) acetyl shikonin, from about 0.05–0.5% (w/w) teracyl shikonin, from about 0.2–1.0% (w/w) hydroxyisovaleryl shikonin, from about 2.5–5.5% (w/w) isobutyl shikonin, and from about 2.5–4.0% (w/w) β,β-dimethylacryl shikonin.

9. A method for the treatment of antibiotic-resistant gram-positive bacterial infections comprising administering to a subject infected with antibiotic-resistant gram-positive bacteria, a pharmaceutically effective amount of a red colored active fraction of a total organic solvent extract from root of Boraginaceae.

10. The method of claim 9, wherein said antibiotic-resistant gram-positive bacteria are selected from the group consisting of antibiotic-resistant *Staphylococcus aureus*, antibiotic-resistant *Enterococcus faecalis*, and antibiotic-resistant *Streptococcus pneumoniae*.

11. The method of claim 9, wherein said red colored active fraction is administered by a mode selected from the group consisting of topical administration and oral administration.

12. The method of claim 11, wherein said pharmaceutically effective amount is about 0.05 to 2.0 mg/cm$^2$ administered topically, and about 0.1 to 7.5 mg/dose administered orally.

13. The method of claim 12, wherein said pharmaceutically effective amount is about 0.2 to 0.5 mg/cm$^2$ administered topically, and about 1.0 to 2.5 mg/dose administered orally.

14. The method of claim 9, wherein said Boraginaceae is a member selected from the group consisting of *Arnebia euchroma*, *Lithospermum erythrorhizon* and *Arnebia guttata*.

15. The method of claim 9, wherein said red colored active fraction comprises from about 0.5–2.5% (w/w) shikonin, from about 18–28% (w/v) acetyl shikonin, from about 0–8.0% (w/w) teracyl shikonin, from about 1.5–15% (w/w) hydroxyisovaleryl shikonin, from about 20–65% (w/w) isobutyl shikonin, and from about 15–45% (w/w) β,β-dimethylacryl shikonin.

16. The method of claim 15, wherein said red colored active fraction comprises from about 1.0–2.0% (w/w) shikonin, from about 20–25% (w/w) acetyl shikonin, from about 0.5–5.0% (w/w) teracyl shikonin, from about 2.0–10% (w/w) hydroxyisovaleryl shikonin, from about 25–55% (w/w) isobutyl shikonin, and from about 25–40% (w/w) β,β-dimethylacryl shikonin.

17. The method of claim 1, wherein said antibiotic-resistant gram-positive bacteria are resistant to an antibiotic selected from the group consisting of streptomycin, tetracycline, erythromycin, and norfloxacin.

18. The method of claim 2, wherein said antibiotic-resistant gram-positive bacteria are resistant to an antibiotic selected from the group consisting of streptomycin, tetracycline, erythromycin, and norfloxacin.

19. The method of claim 9, wherein said antibiotic-resistant gram-positive bacteria are resistant to an antibiotic-selected from the group consisting of streptomycin, tetracycline, erythromycin, and norfloxacin.

20. The method of claim 10, wherein said antibiotic-resistant gram-positive bacteria are resistant to an antibiotic selected from the group consisting of streptomycin, tetracycline, erythromycin, and norfloxacin.

* * * * *